(12) United States Patent
Akers

(10) Patent No.: US 7,231,011 B2
(45) Date of Patent: Jun. 12, 2007

(54) APPARATUS FOR PHOTON ACTIVATION POSITRON ANNIHILATION ANALYSIS

(75) Inventor: Douglas W. Akers, Idaho Falls, ID (US)

(73) Assignee: Battelle Energy Alliance, LLC, Idaho Falls, ID (US)

( * ) Notice: Subject to any disclaimer, the term of this patent is extended or adjusted under 35 U.S.C. 154(b) by 76 days.

(21) Appl. No.: 09/932,531

(22) Filed: Aug. 17, 2001

(65) Prior Publication Data

US 2003/0043951 A1    Mar. 6, 2003

(51) Int. Cl.
*G21G 1/12* (2006.01)
(52) U.S. Cl. ............... 376/157; 250/363.03; 250/358.1
(58) Field of Classification Search ................ 376/157, 376/156; 250/363.03, 358.1, 306, 307
See application file for complete search history.

(56) References Cited

U.S. PATENT DOCUMENTS

| | | | | |
|---|---|---|---|---|
| 3,662,882 | A | * | 5/1972 | Obermayer .................. 378/45 |
| 3,970,855 | A | * | 7/1976 | Holt et al. ................... 250/493 |
| 4,064,438 | A | * | 12/1977 | Alex ........................... 250/308 |
| 4,756,866 | A | * | 7/1988 | Alvarez ....................... 376/157 |
| 4,835,390 | A | * | 5/1989 | Blatchley et al. ......... 250/356.1 |
| 4,980,901 | A | * | 12/1990 | Miller ......................... 378/45 |
| 5,175,756 | A | * | 12/1992 | Pongratz et al. ............. 376/88 |
| 5,200,626 | A | | 4/1993 | Schultz et al. ......... 250/390.04 |
| 5,774,520 | A | * | 6/1998 | Bolotin ........................ 378/50 |
| 6,178,218 | B1 | | 1/2001 | Akers et al. ................ 376/159 |
| 6,236,050 | B1 | | 5/2001 | Tumer |
| 6,639,210 | B2 | | 10/2003 | Odom et al. |
| 6,693,277 | B2 | | 2/2004 | Cowan et al. |
| 2002/0103410 | A1 | * | 8/2002 | Munro et al. .................. 600/3 |
| 2003/0165213 | A1 | | 9/2003 | Maglich et al. |

OTHER PUBLICATIONS

Richard B. Firestone, "The Berkeley Laboratory Isotopes Project, Exploring the Table of Isotopes," (http://ie.lbl.gov/education/isotopes.htm), last updated May 22, 2000, accessed by Examiner on Nov. 10, 2003, 8:51 AM.*
Gedcke, ORTEC AN 59, "How Counting Statistics Controls Detection Limits and Peak Precision", from http://www.ortec-online,com/application-notes/an59.pdf, downloaded Jun. 26, 2004.*
Simon Fraser University Radiation Safety Office, "Radiation Counting STatistics," http://www.sfu.ca/radiation-safety/ststistics.html, downloaded Jun. 26, 2004.*
Simon Fraser University Radiation Safety Office, "Radiation Counting STatistics," http://www.sfu.ca/radiation-safety/ststistics.html, Jul. 7, 2001, downloaded Jun. 26, 2004.*

(Continued)

*Primary Examiner*—Ricardo J. Palabrica
(74) *Attorney, Agent, or Firm*—Fennemore Craig, P.C.

(57) ABSTRACT

Non-destructive testing apparatus according to one embodiment of the invention comprises a photon source. The photon source produces photons having predetermined energies and directs the photons toward a specimen being tested. The photons from the photon source result in the creation of positrons within the specimen being tested. A detector positioned adjacent the specimen being tested detects gamma rays produced by annihilation of positrons with electrons. A data processing system operatively associated with the detector produces output data indicative of a lattice characteristic of the specimen being tested.

19 Claims, 4 Drawing Sheets

OTHER PUBLICATIONS

Wayback Machine, http://web.archive.org, search for publicationdate of information on http://ie.lbl.gov/education/isotopes.htm, accessed Mar. 11, 2005.*

Wayback Machine, http://web.archive.org, search for publicationdate of information on http://www.ortec-online.com, accessed Mar. 11, 2005.*

Wayback Machine, http://web.archive.org, search for publicationdate of information on http://www.sfu.ca/radiation-safety/statistics.html, accessed Mar. 11, 2005.*

Harding et al., "Photon-induced positron annihilation radiation (PIPAR)—A novel gamma-ray imaging technique for radiographically dense materials," Nuclear Instruments and Methods in Physics Research A 398(1997), pp. 409-422.*

Gilboy et al., "On the Potential of Photon Induced Annihilation Photons for Inspection of Engineering Structures," Appl. Radiat. Isot. vol. 48, No. 10-12, pp. 1625-1633.*

Tavora et al., "One-Sided Imaging of Large, Dense Objects Using 511-keV Photons from Induced-Pair Production," IEEE Transactions in Nuclear Science, vol. 45, No. 3, Jun. 1998, pp. 401-406.*

Derlet et al., A positron annihilation lifetime spectroscopy study of porous silicon using a continuous lifetime fitting algorithm, Journal of Materials Science Letters 15 (1996), pp. 1949-1952.*

Banzuch et al., "Study of the Van Cittert and Gold iterative methods of deconvolution and their application in the deconvolution of experimental spectra annihilation," Nuclear Instruments and Methods in Physics Research A 384 (1997), pp. 506-516.*

Zhu et al., "Analysis of positron annihilation lifetime data presented as a sum of convoluted exponentials with the program SPLMOD", Nuclear Instruments and Methods in Physics Research A284 (1989), pp. 443-451.*

Shaffer, Deconvoluted Doppler Broadened Positron Annihilation Spectroscopy: Characterization of Defects in Aluminum, University Microfilms International, 1985.*

Gregory et al., "Analysis of Positron Annihilation Lifetime Data by Numerical Laplace Innversion with Program CONTIN," Nuclear Instruments and Methods in Physics Research A290 (1990), pp. 172-182.*

* cited by examiner

APPARATUS FOR PHOTON ACTIVATION POSITRON ANNIHILATION ANALYSIS

CONTRACTUAL ORIGIN OF THE INVENTION

This invention was made with United States Government support under Contract No. DE-AC07-99ID13727 awarded by the United States Department of Energy. The United States Government has certain rights in the invention.

FIELD OF THE INVENTION

This invention relates generally to non-destructive testing of materials and more specifically to methods and apparatus for performing non-destructive testing of materials using positron annihilation.

BACKGROUND OF THE INVENTION

Non-destructive testing is the name commonly used to identify any of a wide variety of techniques that may be utilized to examine materials for defects without requiring that the materials first be destroyed. Such non-destructive testing of materials is advantageous in that all materials or products may be tested for defects. That is, after testing, acceptable (e.g., substantially defect-free) materials may be placed in service, while the defective materials may be re-worked or scrapped, as may be required. Non-destructive testing techniques are also advantageous in that materials already in service may be tested or examined in-situ, thereby allowing for the early identification of materials or components that may be subject to in-service failure. The ability to test or examine new or in-service materials has made non-destructive testing techniques of extreme importance in safety or failure sensitive technologies, such as, for example, in aviation and space technologies, as well as in nuclear power generation systems.

One type of non-destructive testing technique, generally referred to as positron annihilation, is particularly promising in that it is theoretically capable of detecting fatigue damage in metals at its earliest stages. While many different positron annihilation techniques exist, as will be described below, all involve the detection of positron annihilation events in order to ascertain certain information about the material or object being tested.

In one type of positron annihilation technique, positrons from a radioactive source (e.g., $^{22}$Na, $^{68}$Ge, or $^{58}$Co) are directed towards the material to be tested. Upon reaching the material, the positrons are rapidly "thermalized." That is, the positrons rapidly lose most of their kinetic energy by collisions with ions and free electrons present at or near the surface of the material. After being thermalized, the positrons then annihilate with electrons in the material. During the diffusion process, the positrons are repelled by positively charged nuclei, and thus tend to migrate toward defects such as dislocations in the lattice sites where the distance to positively charged nuclei is greater. In principle, positrons may be trapped at any type of lattice defect having an attractive electronic potential. Most such lattice defects are so-called "open volume" defects and include, without limitation, vacancies, vacancy clusters, vacancy-impurity complexes, dislocations, grain boundaries, voids, and interfaces.

Complete annihilation of a position and an electron occurs when both particles collide and their combined mass is converted into energy in the form of two (and occasionally three) photons (e.g., gamma rays). If the positron and the electron are both at rest at the time of annihilation, the two gamma rays are emitted in exactly opposite directions (e.g., 180° apart) in order to satisfy the requirements of the conservation of momentum. Each annihilation gamma ray has an energy of about 511 keV, the rest energies of an electron and a positron. In positron annihilation techniques nearly all the positrons are at rest in the defect or lattice sites. However, the electrons are not. Therefore, the momentum of the electron tends to determine the momentum of the annihilating pairs and cause the direction of the gamma rays to deviate from 180°. In addition to the momentum constraints, the energies of the gamma rays resulting from the annihilation may deviate slightly from 511 keV, depending on the momentum of the electron. Accordingly, in non-destructive testing techniques utilizing positron annihilation, the detection of the energies and relative angles of the gamma rays produced by the annihilation event are used to derive certain information relating to defects and other characteristics of the material or object being tested.

While positron annihilation techniques of the type described above have been successfully used in the laboratory to detect defects in specimen materials, the technique has not been successfully utilized in field settings. For one thing, the positrons from the external positron source barely penetrate the surface of the material being tested. Consequently, such external positron source techniques are limited to near surface measurements and generally must be conducted under controlled laboratory conditions.

Partly in an effort to solve the depth limitations of the foregoing positron annihilation testing technique, another type of positron annihilation technique has been developed that replaces the external positron source with an external neutron source. Neutrons from the neutron source are directed toward the material being tested. Given sufficient energies, the neutrons will, in certain materials, result in the formation of isotopes that produce positrons. Such isotopes are commonly referred to as positron emitters. The positrons then migrate to lattice defect sites, ultimately annihilating with electrons to produce gamma rays. The resulting gamma rays are thereafter detected in the manner already described in order to derive information relating to the structure of the material being tested.

The foregoing type of positron annihilation system is often referred to as a "neutron activated positron annihilation system" since it utilizes neutrons to trigger or induce the production of positrons. Since neutrons penetrate more deeply into the material being tested than do positrons alone (e.g., from an external positron source), such neutron activated positron annihilation systems are generally capable of detecting flaws deep within the material rather than merely on the surface. Unfortunately, however, only a relatively few elements, such as certain isotopes of copper, cobalt, and zinc, produce positrons in response to the neutron bombardment that are suitable for detecting flaws within the material. Consequently, neutron activated systems are limited to use with materials that contain such responsive elements.

SUMMARY OF THE INVENTION

Non-destructive testing apparatus according to one embodiment of the invention comprises a photon source. The photon source produces photons having predetermined energies and directs the photons toward a specimen being tested. The photons from the photon source result in the creation of positrons within the specimen being tested. A detector positioned adjacent the specimen being tested detects gamma rays produced by annihilation of positrons with electrons. A data processing system operatively associated with the detector produces output data indicative of a lattice characteristic of the specimen being tested.

Also disclosed is a method that comprises the steps of: Producing photons having energies within a predetermined energy range; directing the photons at a specimen to be tested, the photons resulting in the creation of positrons within the specimen being tested; and detecting gamma rays produced by annihilation of positrons with electrons within the specimen.

BRIEF DESCRIPTION OF THE DRAWINGS

Illustrative and presently preferred embodiments of the invention are shown in the accompanying drawing in which.

DETAILED DESCRIPTION OF THE INVENTION

Figure 1:
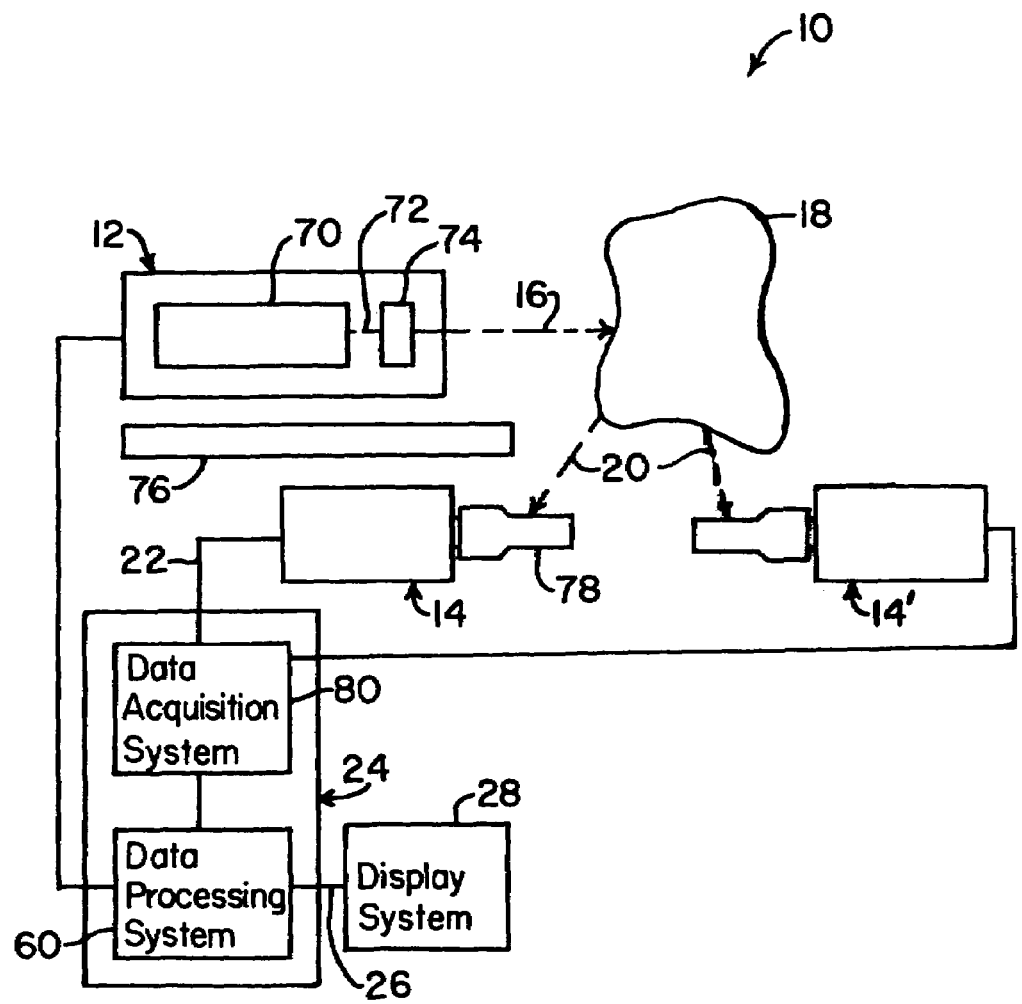
FIG. 1 is a schematic representation of one embodiment of the non-destructive testing apparatus according to the present invention.

Non-destructive testing apparatus 10 according to one embodiment of the present invention is illustrated in FIG. 1 and may comprise a photon source 12 and a detector 14. The photon source 12 produces photons (illustrated schematically by arrow 16) and directs the photons 16 toward a material or specimen 18 being tested. The photons 16 from the photon source 12 activate positron emitters (not shown) within the material or specimen 18, resulting in the creation of positrons (also not shown). Many of the positrons so formed ultimately annihilate with electrons (not shown) within the specimen 18, resulting in the formation of gamma rays (illustrated schematically by arrow 20). The gamma rays 20 resulting from the positron annihilations occurring within the specimen 18 are detected by the detector 14 which produces raw data 22 related to the detected gamma rays 20. A data collection and processing system 24 operatively associated with the detector 14 is responsive to the raw data 22 produced by the detector 14 and processes the raw data 22 to produce output data 26 that are indicative of at least one material characteristic of the specimen 18 being tested. Thereafter, the output data 26 may be presented in human-readable form an a suitable display system 28.

As will be described in greater detail below, the method and apparatus of the present invention are suitable for use with materials or specimens 18 that will produce positrons in response to photon bombardment from the photon source 12. One way for producing positrons involves the decay of neutron-deficient isotopes. In the present invention, the photons 16 from the photon source 12 produce such neutron-deficient isotopes within the specimen 18 by removing or "knocking-off" neutrons from atoms within the specimen 18. The neutron-deficient isotopes (referred to herein in the alternative as "positron emitters") then decay into non-neutron-deficient atoms by the emission of positrons and neutrinos. Consequently, the bombardment of a material or specimen 18 containing certain isotopes amenable to the loss of neutrons by such photon bombardment will result in the formation of positrons within the material or specimen 18. This process is referred to herein as "photo-neutron activation" or, simply, "photon activation." Any material containing isotopes susceptible to such photon activation is suitable for use with the present invention.

Figure 2:
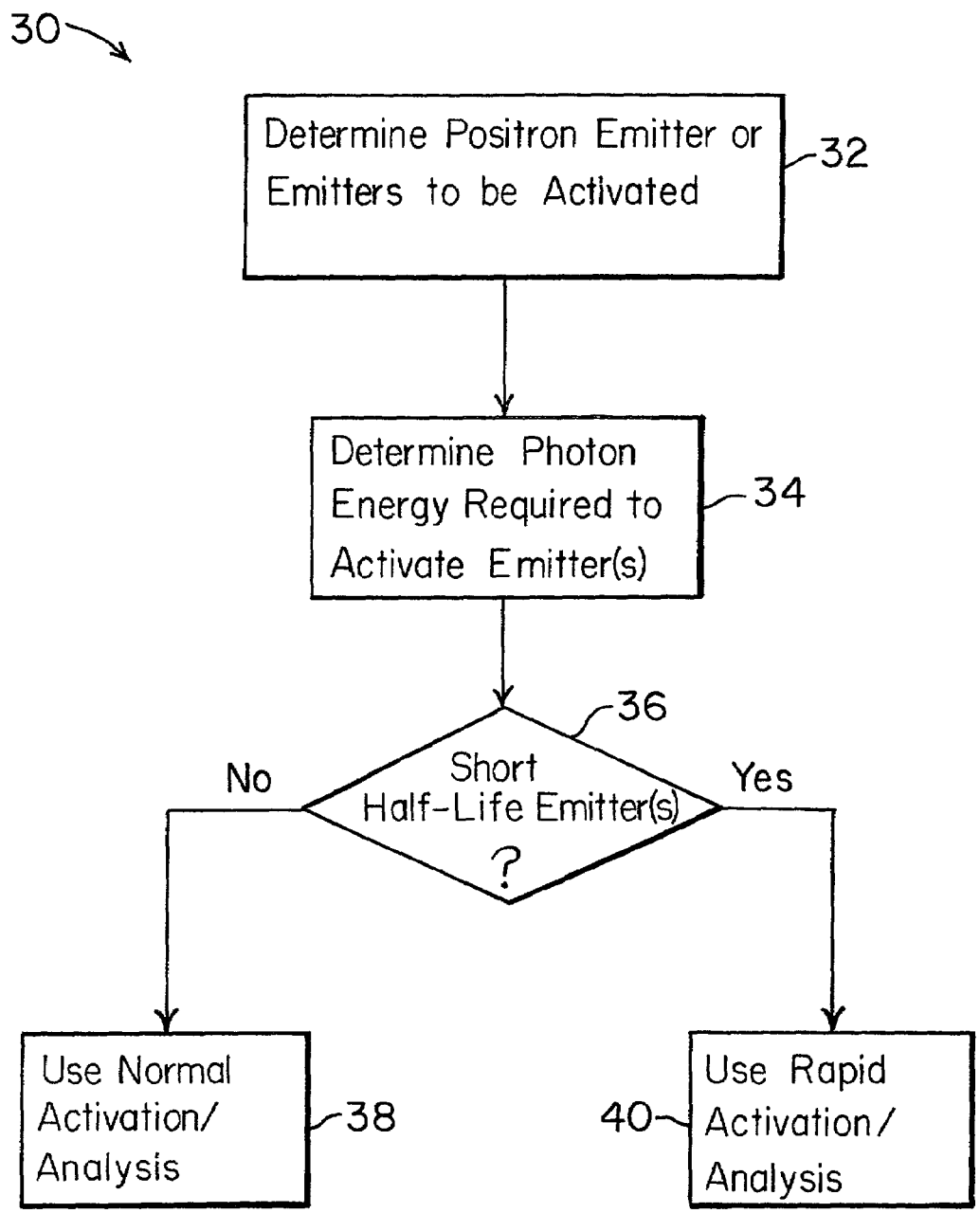
FIG. 2 is a flow chart representation of the method for non-destructive testing according to one embodiment of the present invention.

A method 30 illustrated in FIG. 2 may be used to determine at least one material characteristic of the object or specimen 18. The first step 32 in the method 30 involves determining whether the material or specimen 18 to be analyzed includes one or more isotopes or "positron emitters" that are capable of photon activation. Stated another way, step 32 is used to identify those isotopes contained in the specimen 18 that will produce positrons in response to photon bombardment. A next step 34 in the method 30 determines the photon energy required to activate at least one of the isotopes or positron emitters identified in step 32. As will be described in greater detail below, the method and apparatus of the present invention allow a user to select for activation certain ones of the isotopes or positron emitters comprising the specimen 18. Accordingly, certain isotopes within the specimen 18 may be activated, while leaving other isotopes un-activated. The ability to selectively activate certain positron emitters will allow a user to determine several material characteristics of the specimen 18, including, for example, the amount or quantity of the selected positron emitters present in the specimen 18 as well as the locations of such positron emitters. Such information may be useful in ascertaining a wide range of material characteristics of the specimen 18, as will be described in greater detail below.

Step 36 of the method 30 assesses the half-life of the photon activated isotope or positron emitter to be activated. If the half-life of the positron emitter is greater than a certain time (e.g., typically a few minutes or greater), then the method 30 utilizes a normal activation/analysis process 38 to test the specimen 18. Alternatively, if the half-life of the positron emitter is less than the certain time (e.g., typically on the order of tens of seconds or less), the specimen 18 is tested or analyzed in accordance with a rapid activation/analysis process 40.

Figure 3:
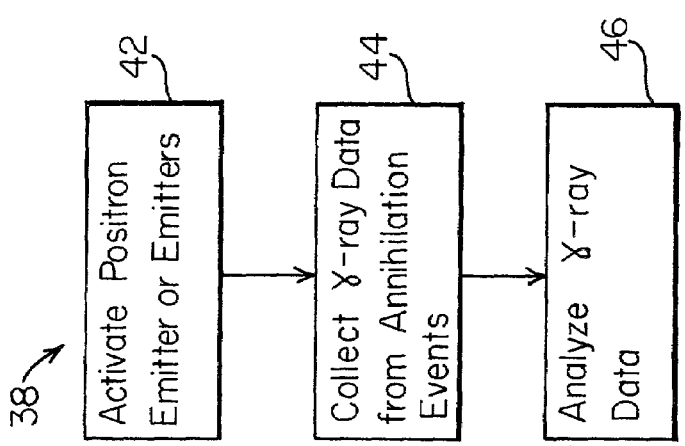
FIG. 3 is a flow chart representation of the normal activation/analysis process.

The normal activation/analysis process 38 is best seen in FIG. 3. A first step 42 in the normal activation/analysis process 38 involves activating the positron emitter or emitters (i.e., the isotope or isotopes identified in step 32). In one preferred embodiment, the positron emitter is activated by bombarding the specimen 18 with photons 16 from the photon source 12. It is generally preferred that the photons 16 from the photon source 12 have sufficient energies to activate the selected isotope or positron emitter. For example, and as will be described in greater detail below, photons having energies in the range of about 8 million electron volts (MeV) to about 22 MeV will activate most of the isotopes (i.e., positron emitters) likely to be found in many common materials. See, for example, Tables I and II. Alternatively, of course, photons having energies either above or below this range may be used, depending on the particular isotope and on the particular material characteristics to be detected.

The photon-activated positron emitters result in the production of positrons within the specimen 18. Such positrons diffuse or migrate through the material comprising specimen 18 and tend to be attracted to voids or other lattice defects having favorable electronic potentials. Ultimately, a significant number of positrons will annihilate with electrons, resulting in the formation of gamma rays 20. Such gamma rays 20 are detected in step 44 by the detector 14, which produces raw data 22. The raw data 22 are then analyzed in step 46 to produce output data 26 that are indicative of at least one material characteristic of the specimen 18. The raw output data 26 may be displayed in suitable form on the display system 28. See FIG. 1.

Figure 4:
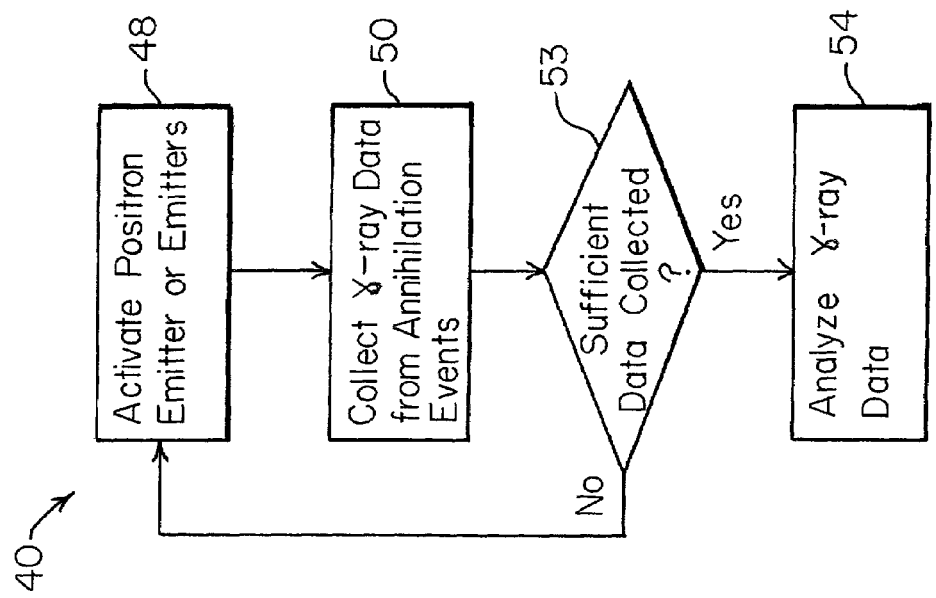
FIG. 4 is a flow chart representation of the rapid activation/analysis process.

If the half life of the isotope or positron emitter to be activated is less than the certain time (e.g., typically on the order of tens of seconds or less), as determined in step 36 (FIG. 2), the method 30 executes the rapid activation/analysis process 40. With reference now to FIG. 4, the rapid activation/analysis process 40 involves alternate photon bombardment and subsequent gamma ray detection of the specimen 18. More specifically, the specimen 18 is first exposed to the photons 16 from the photon source 12 for a selected time (e.g., 10 minutes) at step 48. That is, the positron emitter or emitters are activated. Then, gamma rays 20 resulting from the annihilation of positrons with electrons are detected via detector 14 at step 50. If a sufficient number of gamma rays 20 have been detected, as determined in step 53, the method 30 proceeds to step 54 wherein the data are analyzed to produce output data 26 (FIG. 1) that are indicative of at least one material characteristic of the specimen 18. The output data 26 may be displayed in suitable form on the display system 28. Alternatively, if an adequate number of gamma rays 20 have not been detected, as determined in step 53, the method 30 returns to step 48 wherein the specimen 18 is again exposed to photons 16 from the photon source 12 for the selected time. That is, the positron emitters comprising the specimen 18 are re-activated. The activation and detection steps 48 and 50 are repeated until a sufficient number of gamma rays 20 have been detected.

Figure 5:
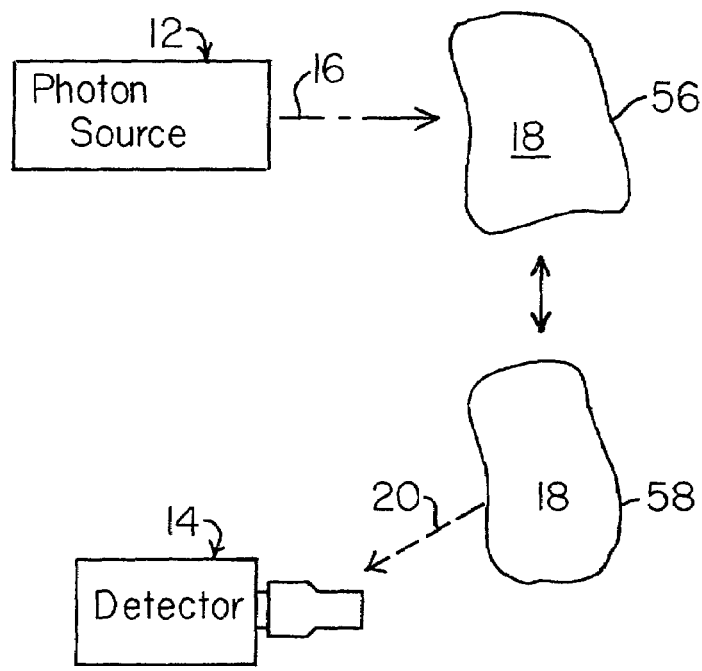
FIG. 5 is a schematic representation of one embodiment of apparatus for performing the rapid activation/analysis process.

The alternate photon activation and detection steps 48 and 50, respectively, may be accomplished in a variety of ways. For example, in one preferred embodiment, the specimen 18 is alternately moved between an activation position 56 and a detection position 58. See FIG. 5. While in the activation position 56, the specimen 18 is positioned adjacent the photon source 12 so that the specimen receives photons 16 therefrom. Then, after having been exposed to the photons 16 for the selected time, the specimen 18 is moved to the detection position 58. While in the detection position 58, the detector 14 detects gamma rays 20 emitted from the specimen 18 as a result of positron/electron annihilations. However, other arrangements are possible for accomplishing the activation and detection steps 48 and 50. For example, in an alternative arrangement, the photon source 12 is alternately energized for the selected time period, then de-energized for a detection time period in which gamma rays 20 emitted from the specimen 18 are detected by the detector 14.

Figure 6:
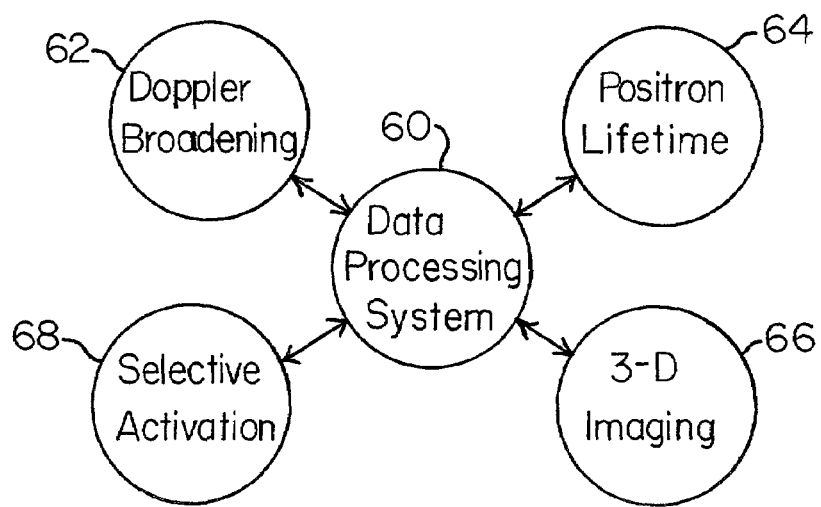
FIG. 6 is a schematic representation of the various algorithms that may be accessed by the data processing system.

Referring now to FIGS. 1 and 6, the data collection and processing system 24 may be provided with a data processing system 60 which processes the raw data 22 from the detector 14 in accordance with one or more algorithms in order to produce the output data 26 which are indicative of at least one material characteristic of the specimen 18. For example, in one preferred embodiment, the data processing system 60 may process the data 22 in accordance with a Doppler broadening algorithm 62, a positron lifetime algorithm 64, and a three-dimensional (3-D) imaging algorithm 66.

The various algorithms (e.g., 62, 64, and 66) process the data 22 from the detector 14 in order to produce output data 26 which are indicative of at least one material characteristic of the specimen 18. For example, the Doppler broadening algorithm 62 is useful in assessing the characteristics of lattice defects contained in the specimen 18, such as, for example, damage resulting from mechanical and thermal fatigue, embrittlement, annealing, or manufacturing defects. The positron lifetime algorithm 64 is also useful in assessing the characteristics of lattice defects. In addition, information obtained from the mean lifetime of various defect components may be used to derive information relating to changing characteristics of the defects present in the specimen 18. The 3-D imaging algorithm 66 may be used to in conjunction with either the Doppler broadening algorithm 62 or the positron lifetime algorithm 64 to produce three-dimensional information regarding locations of the lattice defects contained within the specimen 18. Alternatively, the raw gamma ray data 22 from the detector 14 may be processed in accordance with other algorithms that are now known in the art or that may be developed in the future to derive other types of information, as would be obvious to persons having ordinary skill in the art after having become familiar with the teachings of the present invention. Consequently, the present invention should not be regarded as limited to the particular processing algorithms shown and described herein.

Regardless of the particular algorithm (e.g., 62, 64, or 66) that is used to process the raw data 22, the resulting output data 26 may be presented in human-readable form on a suitable display system 28, such as a CRT or LCD display. Alternatively, other types of display systems may be used to present the output data 26 in useable form.

For each algorithm, e.g., 62, 64, and 66, the data processing system 60 may utilize a selective activation algorithm 68 in which certain isotopes or positron emitters in the specimen 18 are selected to be activated. Stated simply, the selective activation algorithm 68 allows the data processing system 60 to set the energy level of the photons 16 produced by the photon source 12. See FIG. 1. As mentioned above, the selective activation algorithm 68 provides the option to allow the user to activate certain of the isotopes or positron emitters comprising the specimen 18.

A significant advantage of the present invention is that since the positrons are produced within the material or specimen itself, rather than externally, the method and apparatus of the present invention may be used to determine material characteristics of the specimen 18 throughout the thickness (i.e., depth) of the specimen 18. Another significant advantage of the present invention is that it may be used in conjunction with a wide range of materials, including metals, polymers, and composite materials, that were not heretofore available for full depth study by positron annihilation methods.

Still yet other advantages are associated with the ability to produce the positrons within the material specimen itself. For example, the invention realizes increased sensitivity over conventional positron annihilation methods utilizing external positron sources in that there is no extraneous background "noise" caused by annihilations external to the specimen being analyzed. The increased sensitivity also allows other types of detectors (e.g., CdZnTe) to be used. Moreover, the surface of the specimen need not be specially prepared as is typically required with systems involving external positron sources. The analysis techniques herein are also primarily dependent on and sensitive to the atomic characteristics of the specimen 18 and are not dependent on the physical geometry of the specimen.

Another significant advantage of the present invention is that it may be made specific to particular isotopes within the specimen. That is, by adjusting the energies of the photons 16 from the photon source 12, the photons 16 may be used to selectively activate one or more positron emitters within the specimen 18 while leaving other positron emitters un-activated. Moreover, compared with conventional positron annihilation analysis devices, the present invention may be made quite small and portable, thereby allowing the present invention to be readily and easily utilized in field settings to analyze materials and specimens in-situ. The present invention may also be used to monitor materials during production and/or processing, thereby allowing for the early detection of non-compliant materials and for the possibility of adjusting production parameters and processes to minimize the creation of non-compliant materials.

With the foregoing considerations in mind, non-destructive testing apparatus 10 according to one embodiment of the present invention is best seen in FIG. 1 and may comprise a photon source 12 and a detector 14. The photon source 12 produces photons 16 and directs the photons 16 toward the specimen 18 being tested. It is generally preferred, but not required, that the photon source 12 be capable of producing photons 16 having user adjustable (i.e. selectable) energies. The ability to adjust or select the energy of the photons 16 allows a user, in certain situations, to selectively activate only certain ones of positron emitters or isotopes (not shown) comprising specimen 18 while leaving certain other positron emitters un-activated. Alternatively, if such selective activation of the positron emitters is not required or desired in a particular application, the photon source 12 need not be provided with capability to adjust the photon energy.

In one preferred embodiment having the ability to select the energies of the photons 16, the photon source 12 may comprise an electron accelerator 70 for producing a stream of accelerated electrons, shown schematically in FIG. 1 as broken line 72. In order to produce the photons 16 used to bombard the specimen 18, the accelerated electrons 72 are directed toward a target 74 which produces the photons 16 in response to bombardment by the accelerated electron stream 72. Photons generated in this manner are often referred to in the art as bremsstrahlung photons. There is a correlation between the energies of the electrons comprising the electron stream 72 and the photons produced by the target 74 in response to the electron bombardment. Consequently, photons 16 having specified energies can be produced by selecting or adjusting the energies of the electrons contained in the electron stream 72. In the embodiment shown and described herein, the photons 16 produced by the photon source 12 may be selected to have energies in the range of about 8 million electron volts (MeV) to about 22 MeV. Photons 16 having energies in this range are often referred to as gamma rays.

In accordance with the foregoing considerations, then, the electron accelerator 70 may comprise a linear accelerator of the type that are now known in the art or that may be developed in the future that would be suitable for the production of electrons in any of a wide range of energies. By way of example, in one preferred embodiment, the electron accelerator 70 comprises a model 6000 linear accelerator available from Varian Corp. of Palo Alto, Calif. Alternatively, equivalent devices from the same or other manufacturers may also be used. The target 74 which produces the photons 16 may comprise tungsten, although other materials may also be used. Of course, the photon source 12 and/or the various components comprising the photon source 12 (e.g., the electron accelerator 70 and target 74) may be provided with suitable shielding materials (not shown), to prevent the unwanted escape of radiation from the photon source 12.

In another embodiment of the invention, the photon source 12 may comprise a radioactive isotope (not shown) suitable for producing gamma radiation having sufficient energies to activate at least one positron emitter contained in the specimen 18 to be tested. While the use of such an isotopic gamma ray source has the advantage of dispensing with the need for an electron accelerator and target, most isotopic gamma ray sources do not readily lend themselves to producing gamma rays having energies that can be selected and varied by the user. However, the gamma rays produced by certain isotopic sources do have known and generally predictable energies, thus would be suitable for activating positron emitters having threshold (i.e., activation) energies generally at or below the energies of the gamma rays produced by the isotopic gamma ray source.

The detector apparatus 14 may be positioned adjacent the photon source 12 and the specimen 18 so that the detector 14 receives gamma rays 20 resulting from positron/electron annihilation events occurring within the specimen 18. Depending on the geometry of the particular installation, a shield 76 may be positioned between the photon source 12 and the detector 14 to prevent gamma radiation from the photon source 12 from being detected by detector 14. The detector 14 may be provided with a collimator 78 to collimate the gamma rays 20.

The detector 14 may comprise any of a wide range of gamma ray detectors that are now known in the art or that may be developed in the future that are or would be suitable for detecting gamma rays 20 produced by the annihilation of positrons and electrons within the specimen 18. Accordingly, the present invention should not be regarded as limited to any particular type of gamma ray detector. However, by way of example, in one preferred embodiment, the detector 14 may comprise germanium detector of the type that is well-known in the art and readily commercially available. Alternatively, the detector 14 could comprise a cadmium-zinc-tellurium (CdZnTe) detector of the type that is also well-known in the art and readily commercially available. The collimator 78 may comprise a variable slit type or other collimator.

It should also be noted that the present invention is not to be regarded as limited to use with only a single detector. Indeed, many of the algorithms utilized by the present invention require, or at least prefer, the use of more than one detector. For example, the positron lifetime algorithm 64 will generally require the use of at least two detectors (e.g., 14, 14'), one to detect the gamma rays 20 resulting from the annihilation events and one to detect "precursor" radiation associated with the production of the positrons themselves. Similarly, the 3-D imaging algorithm 66 will also generally utilize at least two, and preferably several, gamma ray detectors (e.g., 14, 14') in order to determine the position of the positron/electron annihilation event within the specimen 18. However, since the positron lifetime techniques and 3-D imaging techniques are well-known in the art, as are the requirements for the particular types and positions of detectors (e.g., 14, 14') associated with such techniques, and since such multiple detectors could be easily provided by persons having ordinary skill in the art after having become familiar with the teachings of the present invention, the particular configurations of such multiple detector systems as they could be utilized in the present invention will not be described in further detail herein.

The data acquisition and processing system 24 is operatively associated with the detector apparatus 14 and receives raw data 22 from the detector apparatus 14. In the embodiment shown and described herein, the data acquisition and processing system 24 may comprise a data acquisition system 80, as well as the data processing system 60. The data acquisition system acquires the raw data 22 from the detector and converts it into a form suitable for use by the data processing system 60. For example, in the case where the data processing system 60 comprises a digital computer system, the data acquisition system 80 may include an analog-to-digital (A/D) converter (not shown) suitable for converting the analog data 22 from the detector 14 into digital data suitable for use by the data processing system 60. Of course, other arrangements and configurations are possible, as would be obvious to persons having ordinary skill in the art after having become familiar with the teachings of the present invention. Consequently, the present invention should not be regarded as limited to any particular type of data acquisition system 80. However, by way of example, in one preferred embodiment, the data acquisition system 80 comprises a digital data acquisition system available from EG&G of Oak Ridge, Tenn. as model no. "DSPEC+". Alternatively, similar systems from the same or other manufacturers may also be used. Initial analysis may be performed using the "Gamma Vision" software package commercially available from EG&G or the "Genie 2000" software package commercially available from Canberra of Meriden, Conn. As will be described in greater detail below, in-depth analysis is performed using algorithms to assess peak shape characteristics including shape comparisons, width ratios, and other shape characteristics.

The data processing system 60 may comprise a general purpose programmable digital computer, such as the ubiquitous personal computer, configured to operate in the manner described herein. Alternatively, the data processing system 60 may comprise an application specific computer that is customized to operate in accordance with the teachings herein. Regardless of the particular type of system that is used, the data processing system 60 receives data from the data acquisition system 80 and processes it in order to produce output data 26. The output data 26 may be presented in human-readable form on any of a wide range of devices or systems, such as the display system 28, in order to indicate for the user at least one material characteristic of the specimen 18 being analyzed. By way of example, in one preferred embodiment, the display system 28 may comprise a color display system (such as a CRT or LCD display) that is operatively associated with the data processing system 60. Alternatively, other systems may be used, as would be obvious to persons having ordinary skill in the art.

It is generally preferred, but not required, that the data processing system 60 also be operatively associated with the photon source 12. Such an arrangement allows the data processing system 60 to control the function and operation of the photon source 12, such as, for example, to select the desired photon energy, as well as to activate and deactivate the photon source 12, as may be required by the rapid activation/analysis process 40 (FIGS. 2 and 4) that may be utilized by the method 30 of the present invention. Alternatively, of course, such systems integration need not be provided. For example, the operation of the photon source 12 instead could be manually controlled by the user.

Before proceeding with the description, it should be noted that the method and apparatus of the present invention may be used with materials or specimens 18 that will produce positrons in response to photon bombardment from the photons 16 produced by photon source 12. That is, the specimen 18 should comprise at least one positron emitter that, when "activated," results in the production of positrons within the specimen 18. As mentioned above, one way for generating positrons is through the formation within the specimen 18 of neutron-deficient isotopes, i.e., positron emitters. Such neutron-deficient isotopes generally decay via the emission of positrons and neutrinos. A list of positron emitters, the threshold gamma ray energies required to form or "activate" the positron emitters, as well as their half-lives are presented herein as Tables I and II. Table I includes those isotopes having half-lives on the order of minutes or longer, whereas Table II includes short-lived isotopes having half-lives on the order of tens of seconds or less. It is generally preferred that such short-lived isotopes (i.e., the isotopes listed in Table II) be analyzed with the rapid activation/analysis process 40 shown and described herein.

Tables I and II may be used to readily identify those isotopes that may be converted into positron emitters by photon bombardment as well as to estimate the photon energy required to form the positron emitters.

TABLE I

Positron Emitters

| Element | Reaction | Half-Life | Units | Threshold Energy MeV |
|---|---|---|---|---|
| Chromium | $^{50}Cr \rightarrow ^{49}Cr$ | 42.3 | Minutes | 20.5 |
| Iron | $^{54}Fe \rightarrow ^{53}Fe$ | 8.51 | Minutes | 14 |
| Nickel | $^{58}Ni \rightarrow ^{57}Ni$ | 35.6 | Hours | 12 |
| Copper | $^{65}Cu \rightarrow ^{64}Cu$ | 12.7 | Hours | 8 |
| Copper | $^{63}Cu \rightarrow ^{62}Cu$ | 9.74 | Minutes | 11 |
| Zinc | $^{64}Zn \rightarrow ^{63}Zn$ | 38.5 | Minutes | 20.45 |
| Zirconium | $^{90}Zr \rightarrow ^{89}Zr$ | 4.18 | Minutes | 12.3 |
| Molybdenum | $^{92}Mo \rightarrow ^{91}Mo$ | 1.08, 15.5 | Minutes | 12.5 |
| Tin | $^{112}Sn \rightarrow ^{111}Sn$ | 35 | Minutes | 12.5 |
| Antimony | $^{121}Sb \rightarrow ^{120}Sb$ | 15.9 | Minutes | 10 |
| Titanium | $^{46}Ti \rightarrow ^{45}Ti$ | 3.1 | Hours | 13 |
| Carbon | $^{12}C \rightarrow ^{11}C$ | 20.3 | Minutes | 19 |
| Nitrogen | $^{14}N \rightarrow ^{13}N$ | 9.97 | Minutes | 10.5 |
| Oxygen | $^{15}O \rightarrow ^{14}O$ | 122.2 | Seconds | ND |
| Fluorine | $^{19}F \rightarrow ^{18}F$ | 1.83 | Hours | 20 |
| Phosphorus | $^{31}P \rightarrow ^{30}P$ | 2.5 | Minutes | 10.9 |
| Chlorine | $^{35}Cl \rightarrow ^{34}Cl$ | 32.2 | Minutes | ND |
| Potassium | $^{39}K \rightarrow ^{38}K$ | 7.6 | Minutes | 12.5 |
| Gallium | $^{69}Ga \rightarrow ^{68}Ga$ | 1.13 | Hours | ND |
| Selenium | $^{74}Se \rightarrow ^{73}Se$ | 40 | Minutes | 12 |
| Bromine | $^{79}Br \rightarrow ^{78}Br$ | 6.45 | Minutes | ND |
| Ruthenium | $^{96}Ru \rightarrow ^{95}Ru$ | 1.64 | Hours | ND |
| Palladium | $^{102}Pd \rightarrow ^{101}Pd$ | 8.4 | Hours | ND |
| Silver | $^{107}Ag \rightarrow ^{106}Ag$ | 24 | Minutes | 9.0 |
| Cadmium | $^{106}Cd \rightarrow ^{105}Cd$ | 55.5 | Minutes | ND |
| Indium | $^{113}In \rightarrow ^{112}In$ | 14.4 | Minutes | ND |
| Xenon | $^{124}Xe \rightarrow ^{123}Xe$ | 2 | Hours | ND |
| Cerium | $^{136}Ce \rightarrow ^{135}Ce$ | 17.7 | Minutes | ND |
| Praseodymium | $^{141}Pr \rightarrow ^{140}Pr$ | 40 | Minutes | 7 |
| Neodymium | $^{142}Nd \rightarrow ^{141}Nd$ | 1.04 | Minutes | 9.5 |
| Samarium | $^{144}Sm \rightarrow ^{143}Sm$ | 8.83 | Minutes | 12.5 |
| Europium | $^{151}Eu \rightarrow ^{150}Eu$ | 12.8 | Hours | ND |
| Erbium | $^{164}Er \rightarrow ^{163}Er$ | 1.25 | Hours | ND |

TABLE II

Short Half-Life Positron Emitters

| Element | Reaction | Half-Life | Units | Threshold Energy Mev |
|---|---|---|---|---|
| Neon | $^{20}Ne \rightarrow ^{19}Ne$ | 17.2 | Seconds | ND |
| Magnesium | $^{24}Mg \rightarrow ^{23}Mg$ | 11.32 | Seconds | 16 |
| Aluminum | $^{27}Al \rightarrow ^{26}Al$ | 6.3 | Seconds | ND |
| Silicon | $^{28}Si \rightarrow ^{27}Si$ | 4.14 | Seconds | ND |
| Sulfur | $^{32}S \rightarrow ^{31}S$ | 2.56 | Seconds | 15 |
| Argon | $^{36}Ar \rightarrow ^{35}Ar$ | 1.77 | Seconds | ND |

With reference now to FIG. 2, the method 30 of the present invention may be used to determine at least one material characteristic of the specimen 18. The first step 32 in the method 30 comprises determining whether the material or specimen 18 to be analyzed includes one or more isotopes or "positron emitters" that are capable of photon activation. That is, step 32 involves a determination of the positron emitter or emitters to be activated. Tables I and II may be used for this purpose. For example, if it is known that the specimen 18 contains $^{50}$Cr, photons 16 having sufficient energy may be used to produce or form $^{49}$Cr, a positron emitter.

The next step 34 in the method 30 involves a determination of the photon energy required to activate at least one of the isotopes or positron emitters identified in step 32. For example, $^{50}$Cr has a threshold energy of 20.5 MeV. Therefore, photons 16 having energies greater than or equal to this value will interact with $^{50}$Cr to produce the positron emitter $^{49}$Cr. Of course, photons 16 having energies sufficient to activate chromium-50 will also activate other positron emitters contained in the specimen 18 having lower threshold energies.

Step 36 of the method 30 assesses the half-life of the selected photon activated isotope(s) or positron emitter(s). In this regard it should be noted that if the half-life of the positron emitter is greater than a certain time (e.g., generally on the order of minutes or longer), then it will be advantageous to utilize the normal activation/analysis process 38 to test the specimen 18. Alternatively, if the half-life of the positron emitter is less than the certain time (e.g., on the order of tens of seconds or less), the specimen 18 may be tested or analyzed in accordance with the rapid activation/analysis process 40. In the example discussed herein involving chromium, Table I indicates that the half-life of the positron emitter $^{49}$Cr is about 42.3 minutes. Therefore, it will be preferable to utilize the normal activation/analysis process 38 for this positron emitter.

The normal activation/analysis process 38 is best seen in FIG. 3. The first step 42 in the normal activation/analysis process 38 involves activating the positron emitter (i.e., the isotope or isotopes identified in step 32). In one preferred embodiment, the positron emitter is activated by bombarding the specimen 18 with photons 16 from the photon source 12 having energies sufficient to activate the selected positron emitter or emitters, as the case may be. As mentioned above, photons having energies in the range of about 8 MeV to about 22 MeV will activate most of the isotopes (i.e., positron emitters) likely to be found in many common materials. See, for example, Tables I and II. Alternatively, of course, photons having energies either above or below this range may be used, depending on the particular isotope and on the particular material characteristics to be detected. In the example involving chromium-49, the photons 16 produced by the photon source 12 should have energies of at least 20.5 MeV.

The photon-activated positron emitters result in the production of positrons within the specimen 18. Such positrons diffuse or migrate through the material comprising specimen 18 and tend to be attracted to voids or other lattice defects having a favorable electronic potential. Ultimately, a significant number of the positrons produced by the positron emitter or emitters will annihilate with electrons, resulting in the formation of gamma rays 20. Such gamma rays 20 are detected in step 44 by the detector 14, which produces raw data 22. The raw data 22 are then analyzed in step 46 to produce output data 26 indicative of at least one material characteristic of the specimen 18. The output data 26 may be displayed in suitable form on the display system 28. See FIG. 1.

If the half life of the isotope or positron emitter to be activated is less than a few tens of seconds, as determined in step 36, the method 30 executes the rapid activation/analysis process 40. With reference now to FIG. 4, the rapid activation/analysis process 40 involves alternate photon bombardment and subsequent gamma ray detection of the specimen 18. More specifically, the specimen 18 is first exposed to the photons 16 from the photon source 12 for a selected time at step 48. Then, gamma rays 20 resulting from the annihilation of positrons with electrons are detected via detector 14 at step 50. If a sufficient number of gamma rays 20 have been detected, as determined in step 53, the method 30 proceeds to step 54 wherein the data are analyzed to produce output data 26 (FIG. 1) that are indicative of at least one material characteristic of the specimen 18. The output data 26 may be displayed in suitable form on the display system 28. Alternatively, if an adequate number of gamma rays 20 have not been detected, the method 30 returns to step 48 wherein the specimen 18 is again exposed to photons 16 from the photon source 12 for a selected time. This rapid activation/analysis process 40 is repeated until a sufficient number of gamma rays 20 have been detected.

The alternate photon activation and detection steps 48 and 50, respectively, may be accomplished in a variety of ways. For example, with reference now to FIG. 5, the specimen 18 could be alternately moved between an activation position 56 and a detection position 58. A suitable mechanical arrangement (not shown) may be provided to move the specimen 18 between the activation position 56 and the detection position 58. Alternatively, of course, the specimen 18 could remain stationary while the photon source 12 and detector 14 are moved. Again, a suitable arrangement for so moving the photon source 12 and detector 14 could be easily arrived at by persons having ordinary skill in the art after having become familiar with the teachings of the present invention.

Regardless of the particular arrangement for moving the specimen 18 between the activation position 56 and the detection position 58 (or for moving the photon source 12 and detector 14), the specimen 18, while in the activation position 56, is positioned adjacent the photon source 12 so that the specimen 18 receives photons 16 therefrom. Then, after having been exposed to the photons 16 for the selected time, the specimen 18 is moved to the detection position 58. While in the detection position 58, the detector 14 detects gamma rays 20 emitted from the specimen 18 as a result of positron/electron annihilations. The times in which the specimen 18 is located in the activation position 56 and in the detection position 58 will vary depending on the particular positron emitter or emitters involved and on the particular material characteristics to be studied. However, the time during which the specimen 18 remains in the activation position 56 should be sufficient to activate a sufficient number of positron emitters so that the gamma rays 20 resulting from positron/electron annihilations will be detectable by the detector 14. Similarly, the specimen 18 should remain in the detection position 58 for a time sufficient to detect gamma rays 20 resulting from annihilation events. Generally speaking, the time that the specimen 18 should remain in the detection position 58 should be at least equal to one half-life of the activated positron emitter or emitters, although the time could be longer or shorter than the half-life. In consideration of these matters, then, the present invention should not be regarded as limited to any particular times for each position.

As was briefly mentioned above, other arrangements are possible for alternately activating the positron emitters then detecting the gamma rays 20 resulting from annihilation events. For example, in another arrangement, the photon source 12 is alternately energized for the activation time period, then de-energized for a detection time period in which gamma rays 20 emitted from the specimen 18 are detected by the detector 14. Again, the activation time period should be set so as to activate a sufficient quantity of positron emitters, whereas the detection time period should encompass at least one half-life of the activated positron emitter or emitters.

The data collection and processing system 24 may be provided with a data processing system 60 which may process the data 22 from the detector 14 in accordance with one or more algorithms in order to produce the output data 26 which are indicative of at least one material characteristic of the specimen 18. For example, with reference now to FIG. 6, in one preferred embodiment, the data processing system 60 may process the data 22 in accordance with a Doppler broadening algorithm 62, a positron lifetime algorithm 64, and a three-dimensional (3-D) imaging algorithm 66. The various algorithms (e.g., 62, 64, and 66) process the data 22 from the detector 14 in order to produce output data 26 which are indicative of at least one material characteristic of the specimen 18.

The Doppler broadening algorithm 62 is useful in assessing the characteristics of lattice defects contained in the specimen 18. Such lattice defects may include, without limitation, damage resulting from mechanical and thermal fatigue, embrittlement, annealing, and manufacturing defects. Doppler broadening techniques involve an assessment of the degree of broadening of the 511 keV peak associated with the gamma rays 20 produced by the positron/electron annihilation event. Basically, a broadening of the peak is indicative of the presence of one or more lattice defects. Several different types of Doppler broadening techniques have been developed and are being used in the positron annihilation art and could be easily implemented in the present invention by persons having ordinary skill in the art after having become familiar with the teachings of the present invention. Accordingly, the present invention should not be regarded as limited to any particular type of Doppler broadening technique. However, by way of example, in one preferred embodiment of the invention, the Doppler broadening algorithm 62 may comprise the Doppler broadening algorithm described in U.S. Pat. No. 6,178,218 B1, which is specifically incorporated herein by reference for all that it discloses.

The positron lifetime algorithm 64 is also useful in assessing the characteristics of lattice defects. For example, the positron lifetime algorithm 64 may be used to obtain information as to whether the lattice defects comprise monovacancies, dislocations, slip zones, or particulate inclusions. In addition, information obtained from the mean lifetime of various defect components may be used to derive information relating to changing characteristics of the defects present in the specimen. The positron lifetime algorithm 64 basically involves a determination of the time between positron formation and positron annihilation. In order to do so, the positron lifetime algorithm detects some precursor event associated with the formation of the positron, as well as the gamma rays 20 produced by the positron annihilation event. The time between these two events is the positron lifetime. In accordance with the foregoing process, systems utilizing positron lifetime analysis techniques usually utilize two separate detectors, one for detecting the precursor event and the other for detecting the annihilation event. The system will also usually include constant fraction discriminators, a time amplitude converter, as well as a multichannel analyzer system. However, since systems for detecting positron lifetimes, as well as the algorithms utilized thereby, are well-known in the art and could be easily provided by persons having ordinary skill in the art after having become familiar with the details of the present invention, the positron lifetime algorithm 64, as well as the other systems and detectors that may be required or desired, will not be described in further detail herein.

The 3-D imaging algorithm 66 may be used to in conjunction with either the Doppler broadening algorithm 62 or the positron lifetime algorithm 64 to produce three-dimensional information regarding locations of the lattice defects contained within the specimen 18. That is, in addition to determining the presence and characteristics of lattice defects (e.g., which may be accomplished by either the Doppler broadening algorithm 62 or the positron lifetime algorithm 64), the 3-D imaging algorithm 66 is also able to determine the position within the specimen 18 of the lattice defects. Consequently, the 3-D imaging algorithm 66 is capable of providing a wealth of information regarding the internal structure of the specimen 18.

As mentioned above, the 3-D imaging algorithm 66 will benefit from the use of two or more separate detectors (e.g., detectors 14) in order to accurately define the locations of the positron annihilation events. However, three dimensional imaging techniques of the type that may be utilized in the present invention, as well as multiple detector arrangements for the use of the same, are also well-known in the art and could be readily provided by persons having ordinary skill in the art after having become familiar with the teachings of the present invention. For example, any of the imaging techniques and detector arrangements that are currently utilized in positron emission tomography (PET) may be readily adapted for use with the present invention. Therefore, the particular 3-D imaging algorithm 66 (and detector arrangements) that may be utilized in one embodiment of the present invention will not be described in further detail herein.

For each analysis algorithm, e.g., 62, 64, and 66, described above the data processing system 60 may utilize a selective activation algorithm 68. The selective activation algorithm 68 allows certain isotopes or positron emitters in the specimen 18 to be activated. The selective activation algorithm 68 is responsive to input from the user regarding either the particular positron emitter or emitters to be activated or the desired photon energy. The selective activation algorithm 68 then controls or operates the photon source 12 as necessary to produce photons 16 having energy levels suitable for activating the selected positron emitter or emitters. The selective activation algorithm 68 allows the user to activate certain of the isotopes or positron emitters comprising the specimen 18.

It is contemplated that the inventive concepts herein described may be variously otherwise embodied and it is intended that the appended claims be construed to include alternative embodiments of the invention except insofar as limited by the prior art.

I claim:

1. Non-destructive testing apparatus, comprising:
   a photon source, said photon source producing photons having a predetermined energy and directing the photons toward a specimen being tested, the photons from said photon source resulting in the creation of positrons within the specimen being tested;

a detector positioned adjacent the specimen being tested, said detector producing raw data indicative of a positron annihilation event; and a data processing system operatively associated with said detector and said photon source, said data processing system operating in accordance with a normal activation/analysis process when a half-life of a selected positron emitter within the specimen being tested is greater than a predetermined half-life, said data processing system operating in accordance with a rapid activation/analysis process when a half-life of the selected positron emitter within the specimen being tested is less than the predetermined half-life, said data processing system, when operated in accordance with the rapid activation/analysis process, alternatively activating said photon source and detecting raw data indicative of a positron annihilation event, said data processing system including a Doppler broadening algorithm, said Doppler broadening algorithm processing raw data indicative of a positron annihilation event to produce output data indicative of the presence or absence of a lattice defect in the specimen being tested.

2. The non-destructive testing apparatus of claim 1, wherein said detector produces raw data indicative of a positron formation event, and wherein said data processing system includes a positron lifetime algorithm, said positron lifetime algorithm processing raw data indicative of a positron formation event to produce output data indicative of a changing presence or absence of a lattice defect.

3. The non-destructive testing apparatus of claim 1, further comprising a second detector positioned adjacent the specimen being tested, said second detector producing raw data indicative of a positron formation event, wherein said data processing system includes a positron lifetime algorithm, said positron lifetime algorithm processing data indicative of a positron formation event to produce output data indicative of a changing presence or absence of a lattice defect.

4. The non-destructive testing apparatus of claim 1, wherein said data processing system includes a selective activation algorithm, said selective activation algorithm responsive to a user input, said selective activation algorithm operating said photon source to produce photons having the predetermined energies in response to the user input.

5. The non-destructive testing apparatus of claim 1, wherein said data processing system includes a three-dimensional imaging algorithm, said three-dimensional imaging algorithm processing raw data indicative of a positron annihilation event to produce output data indicative of a location of the presence or absence of a lattice defect within the specimen being tested.

6. Non-destructive testing apparatus, comprising:
positron activation means for activating a positron emitter within a specimen being tested;
detector means for detecting a positron annihilation event within the specimen being tested and for producing raw data indicative of the positron annihilation event;
means for alternately activating the positron emitter within the specimen being tested and detecting a positron annihilation event; and
data processing means operatively associated with said detector means, said data processing means processing raw data indicative of the positron annihilation event in accordance with a Doppler broadening algorithm to produce output data indicative of the presence or absence of a lattice defect in the specimen being tested.

7. The non-destructive testing apparatus of claim 6, wherein said detector means detects a positron formation event and a positron annihilation event and produces raw data indicative of the positron formation event and the positron annihilation event, and wherein said data processing means processes raw data indicative of the positron formation event in accordance with a positron lifetime algorithm to produce output data indicative of a changing presence or absence of a lattice defect.

8. The non-destructive testing apparatus of claim 6, further comprising second detector means for detecting a positron formation event and for producing raw data indicative of the positron formation event, wherein said data processing means processes raw data indicative of the positron formation event in accordance with a positron lifetime algorithm to produce output data indicative of a changing presence or absence of a lattice defect.

9. The non-destructive testing apparatus of claim 6, wherein said means for alternately activating the positron emitter within the specimen being tested and detecting a positron annihilation event comprises means for moving the specimen being tested between an activation position and a detection position.

10. Non-destructive testing apparatus, comprising:
a photon source, said photon source producing photons having a predetermined energy and directing the photons toward a specimen being tested, the photons from said photon source resulting in the creation of positrons within the specimen being tested;
a detector positioned adjacent the specimen being tested, said detector producing raw data related to a positron annihilation event; and
a Doppler broadening processor operatively associated with said detector and responsive to the raw data produced thereby, said Doppler broadening processor producing output data indicative of the presence or absence of a lattice defect in the specimen being tested.

11. The non-destructive testing apparatus of claim 10, further comprising three-dimensional imaging apparatus operatively associated with said detector and responsive to the raw data produced thereby, said three-dimensional imaging apparatus producing output data indicative of a location of the presence or absence of a lattice defect within the specimen being tested.

12. The non-destructive testing apparatus of claim 10, wherein said detector produces raw data that include data indicative of a positron formation event and data indicative of a positron annihilation event, said non-destructive testing apparatus further comprising a positron lifetime processor operatively associated with said detector and responsive to the raw data produced thereby, said positron lifetime processor producing output data indicative of the presence or absence of a lattice defect of the specimen being tested and indicative of a changing presence or absence of a lattice defect.

13. Non-destructive testing apparatus, comprising:
a photon source, said photon source producing photons having a predetermined energy and directing the photons toward a specimen being tested, the photons from said photon source resulting in the creation of positrons within the specimen being tested;
a detector positioned adjacent the specimen being tested, said detector producing raw data indicative of a positron formation event and a positron annihilation event; and a positron lifetime processor operatively associated with said detector and responsive to the raw data produced thereby, said positron lifetime processor producing output data indicative of a the presence or absence of a lattice defect in the specimen being tested and indicative of a changing presence or absence of a lattice defect.

14. The non-destructive testing apparatus of claim 13, further comprising three-dimensional imaging apparatus operatively associated with said detector and responsive to the raw data produced thereby, said three-dimensional imaging apparatus producing output data indicative of a location of the presence or absence of a lattice defect within the specimen being tested.

15. Non-destructive testing apparatus, comprising:
a photon source, said photon source producing photons having a predetermined energy and directing the photons toward a specimen being tested, the photons from said photon source resulting in the creation of positrons within the specimen being tested;
a detector positioned adjacent the specimen being tested, said detector producing raw data indicative of a positron formation event and a positron annihilation event; and
a data processing system operatively associated with said detector, said data processing system including:
a Doppler broadening algorithm, said Doppler broadening algorithm processing raw data indicative of a positron annihilation event to produce output data indicative of a presence or absence of a lattice defect in the specimen being tested;
a positron lifetime algorithm, said positron lifetime algorithm processing raw data indicative of a positron formation event to produce output data indicative of a changing presence or absence of a lattice defect; and
a three-dimensional imaging algorithm, said three-dimensional imaging algorithm processing raw data indicative of a positron annihilation event to produce output data indicative of a location of the presence or absence of a lattice defect within the specimen being tested.

16. Non-destructive testing apparatus, comprising:
a photon source, said photon source producing photons having a predetermined energy and directing the photons toward a specimen being tested, the photons from said photon source resulting in the creation of positrons within the specimen being tested;
a detector positioned adjacent the specimen being tested, said detector producing raw data indicative of a positron annihilation event; and
a data processing system operatively associated with said detector and said photon source, said data processing system including:
a Doppler broadening algorithm, said Doppler broadening algorithm processing raw data indicative of a positron annihilation event to produce output data indicative of a presence or absence of a lattice defect in the specimen being tested; and
a positron lifetime algorithm, said positron lifetime algorithm processing raw data indicative of a positron formation event to produce output data indicative of a changing presence or absence of a lattice defect,
said data processing system operating in accordance with a normal activation/analysis process when a half-life of a selected positron emitter within the specimen being tested is greater than a predetermined half-life, said data processing system operating in accordance with a rapid activation/analysis process when a half-life of the selected positron emitter within the specimen being tested is less than the predetermined half-life, said data processing system, when operated in accordance with the rapid activation/analysis process, alternatively activating said photon source and detecting raw data indicative of a positron annihilation event, said data processing system using said Doppler broadening algorithm and said positron lifetime algorithm to process raw data indicative of a positron annihilation event and produce output data indicative of the presence or absence of a lattice defect in the specimen being tested.

17. The non-destructive testing apparatus of claim 16, wherein said data processing system further comprises a three-dimensional imaging algorithm and wherein said data processing system uses said three-dimensional imaging algorithm to produce output data indicative of a location of the presence or absence of a lattice defect within the specimen being tested.

18. The non-destructive testing apparatus of claim 1, further comprising means for alternately moving the specimen between an activation position and a detection position, the activation position being adjacent said photon source, the detection position being adjacent said detector.

19. The non-destructive testing apparatus of claim 1, further comprising means for alternately moving said photon source adjacent the specimen during the activation time and away from the specimen during the detection time and for alternately moving said detector adjacent the specimen during the detection time and away from the specimen during the activation time.

* * * * *